US008480640B2

(12) United States Patent
Santimaw

(10) Patent No.: US 8,480,640 B2
(45) Date of Patent: Jul. 9, 2013

(54) NONINVASIVE BODILY WASTE COLLECTION SYSTEM AND METHODS OF USE

(76) Inventor: Robert J. Santimaw, Charlotte, NC (US)

( * ) Notice: Subject to any disclaimer, the term of this patent is extended or adjusted under 35 U.S.C. 154(b) by 436 days.

(21) Appl. No.: 12/471,336

(22) Filed: May 22, 2009

(65) Prior Publication Data

US 2010/0298789 A1 Nov. 25, 2010

(51) Int. Cl.
*A61M 1/00* (2006.01)
(52) U.S. Cl.
USPC ............................................ 604/317; 604/332
(58) Field of Classification Search
USPC .......... 604/317, 319, 332, 338, 339, 342–344
See application file for complete search history.

(56) References Cited

U.S. PATENT DOCUMENTS

| 3,522,807 | A | 8/1970 | Millenbach |
| 3,804,093 | A | 4/1974 | Fell |
| 4,030,500 | A | 6/1977 | Ronnquist |
| 4,368,733 | A | 1/1983 | Sanidas |
| 4,654,037 | A | 3/1987 | Fenton |
| 5,312,384 | A | 5/1994 | Temple |
| 5,330,447 | A | 7/1994 | Barth |
| 5,421,827 | A | 6/1995 | Temple |
| 5,470,325 | A | 11/1995 | Fundock |
| 5,593,397 | A | 1/1997 | La Gro |
| 6,132,408 | A | 10/2000 | Lutz |
| 6,595,971 | B1 | 7/2003 | von Dyck et al. |
| 6,984,226 | B1 | 1/2006 | Abell et al. |
| 7,722,583 | B2 * | 5/2010 | Kim et al. ..................... 604/317 |
| 2007/0049906 | A1 * | 3/2007 | Magnusson ................... 604/540 |
| 2008/0287920 | A1 * | 11/2008 | Fangrow et al. .............. 604/535 |
| 2010/0160875 | A1 * | 6/2010 | James .......................... 604/319 |

OTHER PUBLICATIONS

Beniamino Palmieri, et al., Ostomy/Wound Management, ISSN: 0889-5899, vol. 51, Issue 12, Dec. 2005, pp. 44-52.
www.medicaldelivered.com/drainable-fecal-collectors-box-of-10-p-37913.html, Web-page Drainable Fecal Collectors, Hollister. Model: HOL9821_BX10, effective date unknown.

\* cited by examiner

*Primary Examiner* — Melanie Hand
(74) *Attorney, Agent, or Firm* — Everman Law Firm, PA; Gregory R. Everman

(57) ABSTRACT

A noninvasive bodily waste collection system for removing gas, solid or liquid body waste products collected from a peri-anal or stoma of the person to a suction device. The system includes a collection bag having a wafer for adhesive attachment to a person, an evacuation tube within the collection bag and having a plurality of openings for receiving waste from the collection bag, a suction tube attached to the evacuation tube for evacuating waste from the collection bag, and a suction device which provides the necessary vacuum pressure to automatically draw waste out of the collection bag. At least a portion of the evacuation tube is attached to the collection bag such that the tube cannot freely move within the bag and that the proximal end of the evacuation tube can be located in a desired position.

17 Claims, 8 Drawing Sheets

NONINVASIVE BODILY WASTE COLLECTION SYSTEM AND METHODS OF USE

BACKGROUND OF THE INVENTION

1. Field of the Invention

The present invention relates to a bodily waste collection system that uses a noninvasive method of adhering an apparatus in the form of a bag to a person and has a self-contained collection tube for removing gas, solid or liquid body waste products collected from a peri-anal or stoma of the person to a suction device.

2. Description of the Related Art

Bedridden patients in hospitals, elderly in nursing homes, and others may have certain medical conditions in which it is necessary to collect and dispose of fecal matter and other bodily discharged waste matters. A conventionally known method for this purpose is an indwelling system wherein a tube is inserted into a patient's rectum. However, due to the invasive nature of this method, there are many drawbacks. First, a doctor's order is required to perform this procedure. Additionally, this method may not be suitable when a patient is experiencing rectum bleeding and can be uncomfortable to the patient. The method also makes it more difficult to determine whether a medical concern such as rectal bleeding is occurring.

Fecal collection bags are also known for the collection and ultimately the disposal of anally discharged waste matters. Fecal bags are advantageous in some regards over indwelling systems in that they are adhesively attached to the peri-anal area of a person without having any component thereof being inserted into the rectum. As such, a nurse can perform this task without first obtaining a doctor's order and the procedure is less costly than an indwelling system. There is also less risk to the person as the procedure is not invasive and does not interfere with determining whether the person is experiencing rectal bleeding.

Notwithstanding, fecal bags have some inherent disadvantages. First, the method of emptying the bag is to remove the bag from the patient and manually push fecal and other matter out of the bag. Needless to say, this is a mal-odorous and unpleasant task.

Another problem is that waste matter collected in the fecal bag and associated gases may irritate a person's skin. Also, as fecal bags must be frequently removed from the body for cleaning, the peri-anal region may become irritated by constant removal and reattachment of the adhesively mounted bags. Fecal bags also may occasionally leak or otherwise loose their seal to the person thereby causing an odor nuisance or mess. Capture matter and the generated gases can perpetuate possible leakage by breaking down the adhesive contact between the fecal bag and person.

An example of a fecal collector device is described in U.S. Pat. No. 5,593,397, to La Gro. The fecal collector includes a bag made of elastomeric heat-sealable film having an opening for receiving fecal discharge and a thin attachment patch having a central opening in register with the opening of the bag. Other patents illustrative of the art of fecal collectors adapted for peri-anal attachment include U.S. Pat. No. 3,522,807, to Millenbach; U.S. Pat. No. 3,804,093 to Fell; U.S. Pat. No. 4,368,733 to Sanidas; U.S. Pat. No. 4,445,898 to Jensen; U.S. Pat. No. 5,312,384 to Temple; and U.S. Pat. No. 5,421,827 to Temple.

A similar device to a fecal bag is an ostomy bag. An ostomy bag is another type collection bag used to capture bodily waste products, but wherein the waste products are being passed through a stoma. During a surgical procedure known as an ostomy, a portion of the colon is attached to a bodily opening formed in the abdominal wall referred to as a stoma. The most common types of ostomy include colostomy, ileostomy, and urostomy, depending on what part of the intestines or the bladder is removed. The stoma does not have a sphincter muscle for contraction and closing the bodily opening; as a result, some form of device, such as an ostomy bag, is required to be worn over the stoma to collect bodily waste products and to retain them until the bag can be removed and cleaned or replaced. An ostomy bag has many of the same disadvantages as described in regards to the aforementioned fecal bag.

Various improvement have been made to conventional ostomy bags in an attempt to overcome their various disadvantages. One such example is U.S. Pat. No. 4,654,037, to Fenton, which describes an ostomy pouch having a fluid distribution tube connected to a source of cleansing fluid for cleaning the pouch. Other examples include U.S. Pat. No. 6,132,408, to Lutz, which describes a drainage system for a urostomy bag having an external drainage tube with a connector at one end and a clamp at the opposite discharge end; U.S. Pat. No. 5,330,447, to Barth, which discloses a irrigator for colostomy patients having a drainage line connected to a bag and a pump connected to an air chamber for pressurizing the bag; and U.S. Pat. No. 5,470,325, to Fundock, which is directed to an ostomy bag having a hose coupled to an opening for venting purposes. Notwithstanding, ongoing advancements in the art, the problems of odor, waste removal from the bag, handling of a soiled bag and patient health and comfort persist.

Accordingly, there is a need in the art for continued improvement to fecal and ostomy bags. In particular, there is a need in the art for a bodily waste collection system that is non-invasive and automatically-emptying. Additionally, there is a need in the art of a bodily waste collection system that may be applied by a nurse without requiring a doctor's order and does not interfere with observing whether a person has rectal bleeding. Further, there is a need in the art for a bodily waste collection system that reduces odors, leakages and person discomfort as compared to conventional devices. With an objective towards overcoming and avoiding problems associated with conventional fecal and ostomy devices, the following described noninvasive bodily waste collection system has been developed.

BRIEF SUMMARY OF THE INVENTION

The present invention overcomes many disadvantages of conventional devices by providing a noninvasive bodily waste collection system for removing gas, solid or liquid body waste products collected from a peri-anal or stoma of the person to a suction device. Generally, the system includes a collection bag having a wafer for adhesive attachment to a person, an evacuation tube within the collection bag and having a plurality of openings for receiving waste from the collection bag, a suction tube attached to the evacuation tube for evacuating waste from the collection bag, and a suction device which provides the necessary vacuum pressure to automatically draw waste out of the collection bag. At least a portion of the evacuation tube is attached to the collection bag such that the tube cannot freely move within the bag and that the proximal end of the evacuation tube can be located in a desired position. Optionally, the tube is attached to the collection bag in a manner whereby bodily waste does not get trapped between the tube and collection whereat it would otherwise be more difficult to remove from the bag.

In accordance with an embodiment of the present invention a noninvasive bodily waste collection apparatus is describe having a collection bag which defines an interior chamber and has first and second openings. A wafer is attached to said collection bag and has an orifice that coincides with the first opening of the bag. The wafer is releasably attachable to a person by adhesive contact at a position, such as the peri-anal region, whereby waste from the person is passed through the first opening and orifice and into the interior chamber. An evacuation tube having first and second sections is provided to evacuate waste for the collection bag. The first section of the evacuation tube is provided with at least one opening and more preferably a plurality of openings which communicate with the interior chamber of the bag so that waste may pass from the interior chamber into the evacuation tube. At least a portion of the first section is directly attached to the collection bag and, by doing so, that portion is fixed in a position relative to the collection bag. A suction device, having a suction tube attached to the evacuation tube suction, provides vacuum pressure to draw waste from the interior chamber, through the evacuation and suction tubes, to a container for storage, testing and disposal. In specific embodiments of the present invention, at least 25%, more preferably at least 50% and most preferably at least 75% of the first section is directly attached to the collection bag. In another embodiment, no more than 90%, more preferably no more than 75% and most preferably no more than 50% of the first section is exposed to the interior chamber of the collection bag. In still another alternative embodiment, the proximal end of the evacuation tube is not directly attached to said collection bag and its terminal end is positioned about one to three inches from a center of said first opening.

In accordance with another embodiment of the present invention, a method of using a noninvasive bodily waste collection system is described. The method includes the steps of providing a bodily waste collection system, having a collection bag defining an interior chamber and having first and second openings, a wafer attached to the collection bag and having an orifice that coincides with the first opening, an evacuation tube having first and second sections wherein at least a portion of the first section is directly attached to the collection bag whereby that portion is fixed in position relative to the collection bag. A suction device having a suction tube is attached to the evacuation tube for drawing waste from the interior chamber and through the evacuation and suction tubes. The steps further include attaching the wafer to the person at a location that is noninvasive, such the peri-anal region of the person, passing waste from the person through the first opening and orifice and into the interior chamber, applying vacuum pressure via the suction device to the suction tube, evacuation tube and interior chamber, drawing waste under vacuum pressure from the interior chamber, through at least one opening of the evacuation tube and into the evacuation tube, and drawing waste under vacuum pressure from the evacuation tube and into the suction tube and ultimately into container where it can be tested and/or disposed of. In a specific embodiment, at least 25% of the first section of the evacuation tube is directly attached to the collection bag.

BRIEF DESCRIPTION OF THE SEVERAL VIEWS OF THE DRAWING

The above described and other features, aspects, and advantages of the present invention are better understood when the following detailed description of the invention is read with reference to the accompanying drawings, wherein.

DETAILED DESCRIPTION OF THE INVENTION

The present invention will now be described more fully hereinafter with reference to the accompanying drawings in which preferred embodiments of the invention are shown. This invention may, however, be embodied in many different forms and should not be considered as limited to the embodiments set forth herein. These exemplary embodiments are provided so that this disclosure will be both thorough and complete, and will fully convey the scope of the invention to those skilled in the art.

Figure 1:
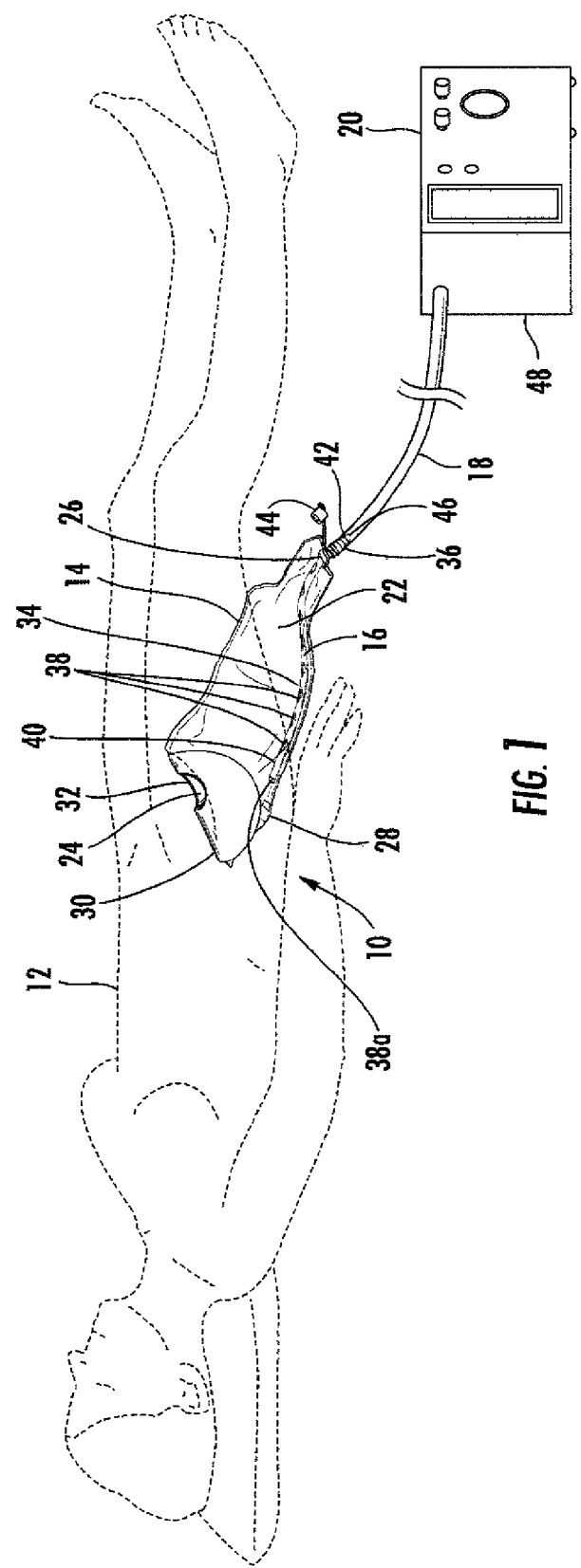
FIG. 1 is a perspective view of a bodily waste collection system, in use attached to a person in a supine position, in accordance with an exemplary embodiment of the present invention.
Figure 2:
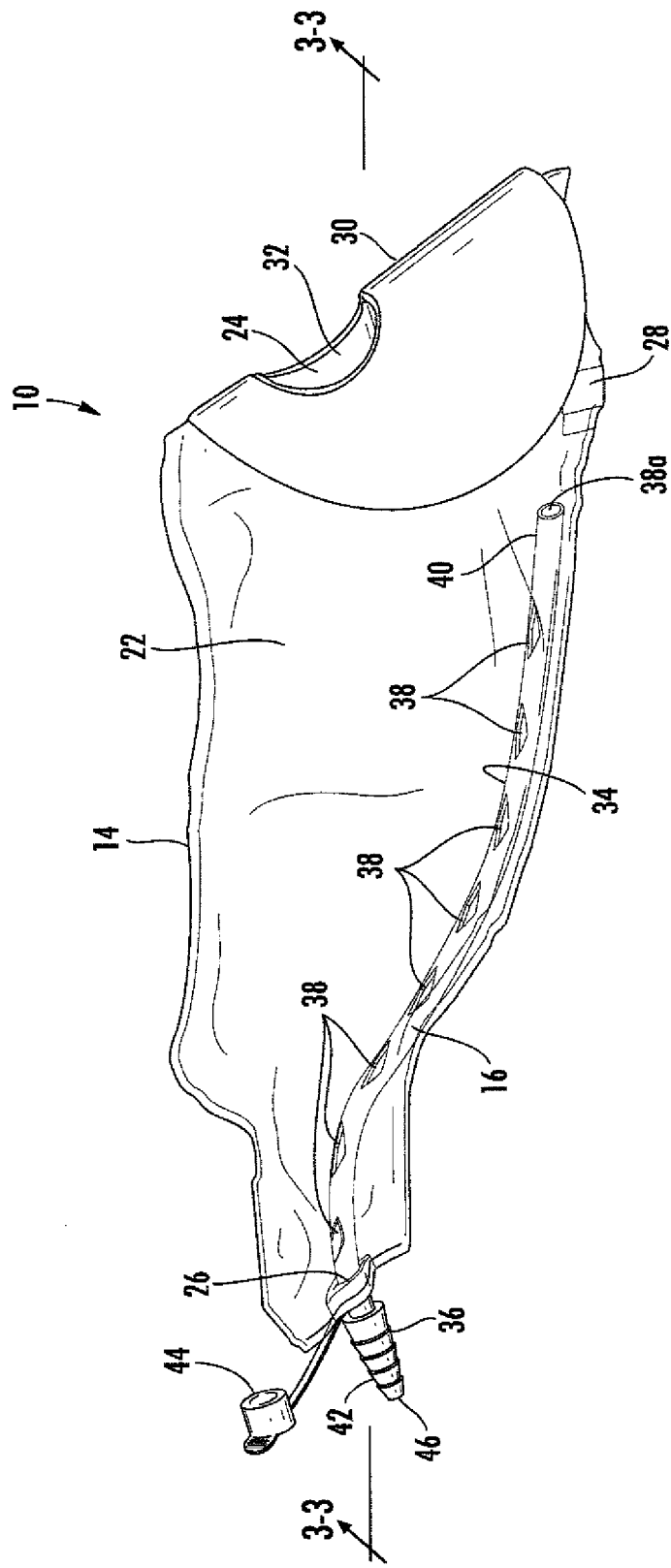
FIG. 2 is a side view of the bodily waste collection system of FIG. 1.
Figure 3:
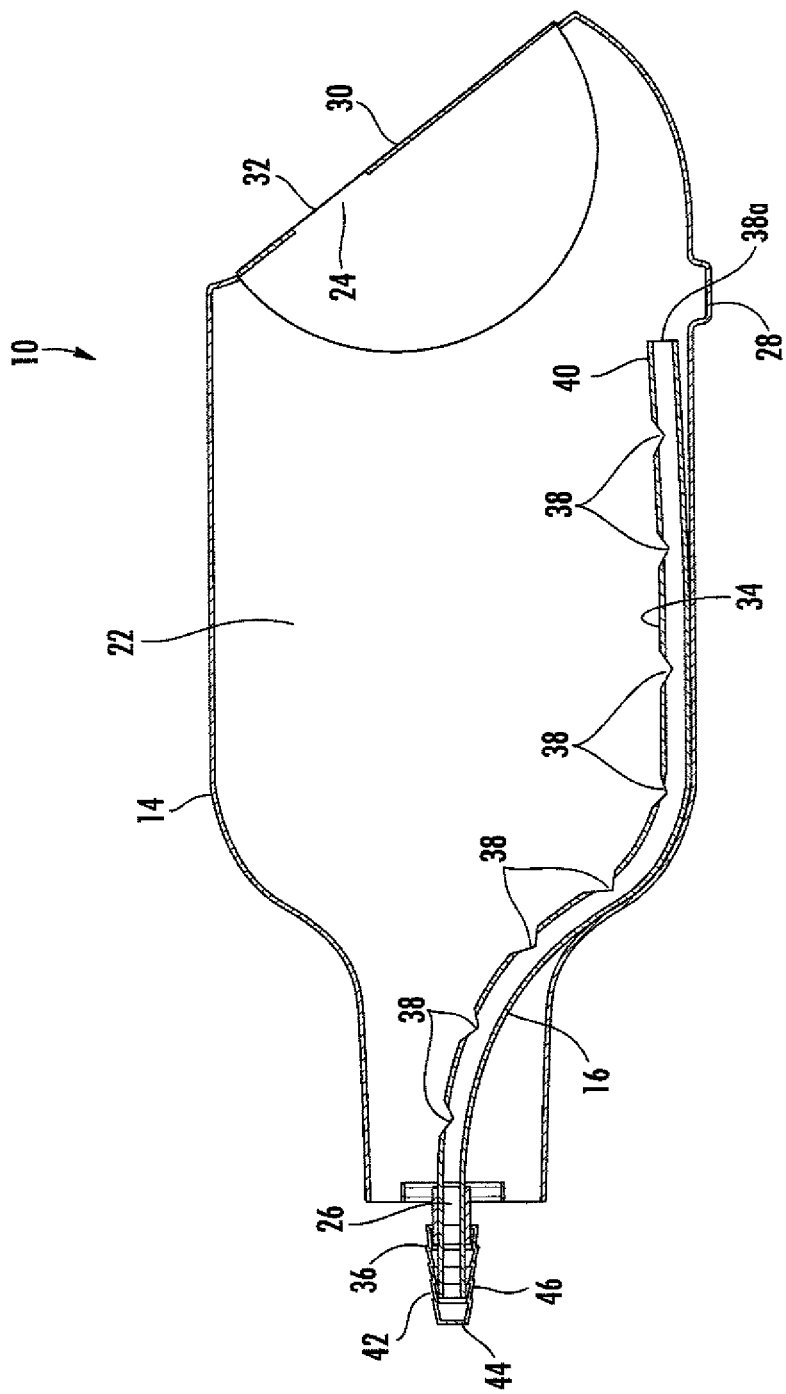
FIG. 3 is cross-sectional view for the waste collection system, taken from sectional line 3-3 of FIG. 2.

Referring now to the drawings, and particularly to FIGS. 1-3, the present invention is a non-invasive bodily waste collection system 10 that is configured to remove and collect waste discharged from a person 12 (FIG. 1). As used herein, the term "waste" refers to gas, solid and/or liquid bodily waste products from a person 12.

The bodily waste collection system 10 has particular utility when used to collect waste discharged through a person's anus. Additionally, the waste collection system 10 may also have application as applied to a stoma (not illustrated herein). Although the collection system 10 may be used for a variety of medical purposes, it will be described herein in accordance with its principal use as attached to a person's peri-anal region.

The waste collection system 10 includes a collection bag 14, an evacuation tube 16 disposed at least partially within the bag 14, a suction tube 18 attached to the evacuation tube 16 for evacuating waste from the collection bag 14, and a suction device 20 which provides the necessary vacuum pressure to automatically draw waste out of the collection bag 14.

The collection bag 14 defines an interior chamber 22 and has a first opening 24 at its proximal end which is adapted to receive waste from a person's anus, a second opening 26 at its distal end which allows for waste to pass from the collection bag 14 to the suction device 20, and a sample port 28 to allow access into the interior chamber 22 for testing of the waste. The waste collection bag 14 is made of a suitable elastomeric material of the type commonly used in conventional fecal bags, such as the fecal bag sold by Hollister, Inc.

A wafer 30 having an orifice 32 is attached to the collection bag 14 such that the wafer orifice 32 and the first opening 24 of the collection bag 14 preferably coincide with each other. The wafer is provided with an adhesive for releasable securement of the collection bag 14 to the peri-anal region of a person 12. The wafer orifice 32 and first opening 24 are positioned in alignment with the anus such that waste discharge from the anus passes through the orifice 32 and opening 24 and into the collection bag 14. The wafer may be of a known configuration, such as those wafers currently used with conventional fecal bags sold by Hollister, Inc.

The evacuation tube 16 has a first section 34 that is positioned within the collection bag 14 in order to withdrawal waste previously discharged therein and a second section 36 that extends outwardly from the second opening 26 of the bag 14 for connection to the suction tube 18.

The first section 34 is provided with at least one opening and, more preferably a plurality of openings 38, which communicate with the interior chamber 22 of the bag 14 for receiving waste into the evacuation tube 16. In the preferred embodiment, the openings 38 comprise an opening 38a at the proximal end of the evacuation tube 16 and openings 38 intermittently positioned along the length of the first section 34. The openings are may be of any suitable number, size or shape that allows for successful evacuate of waste from the collection bag 14. That is, the openings are of sufficient size to allow matter to be sucked into the evacuation tube 16, maintain proper suction pressure, and achieve waste removal throughout the collection bag 14.

Measured as a percentage of length, at least a portion, more preferably at least 25%, even more preferably at least 50%, and most preferably at least 75% of the first section 34 is directly attached to the collection bag 14 in order to maintain the attached portion of the evacuation tube 16 in a fixed positioned relative to the collection bag 14. By fixing the position of the evacuation tube 16 within the collection bag 16, ideal positioning of the tube 16 may be maintained and concerns of the tube inadvertently engaging the person 12 are obviated.

Ideally, the tube 16 is fixed along the bottom of the collection bag 14, taken from the view point of when the bag 14 is properly attached to a person 12 in supine position, whereby waste is assisted towards the evacuation tube 16 by gravity. Also, by fixing the position of the tube 16, the openings 38 may be maintained at a desired orientation, such as the illustrated upward facing direction. Additionally, by fixing the evacuation tube 16, the tube 16 cannot be pushed further into the bag 14 or become orientated in a position that could jab the person 12.

The second section 36 of the evacuation tube 16 extends through the second opening 26 of the bag 14 for being releasably connected to the suction tube 18. The second section 36 has a ribbed male fitting 42 over which the suction tube 18 slides for attachment thereto. Numerous other well-known means of releasably connecting together the evacuation and suction tubes 16, 18 may also be used. Optionally, a cap 44 is provided to seal off the distal end 46 of the tube when the bag 14 is not connected to the suction tube 18.

The suction tube 18 is connectable to a suction device 20, such as a centralized wall suction system as readily available in hospitals. The suction device 20 provides the necessary vacuum pressure to move the waste from the bag to a container 48 whereat the waste is collected for testing or disposal.

Figure 4:
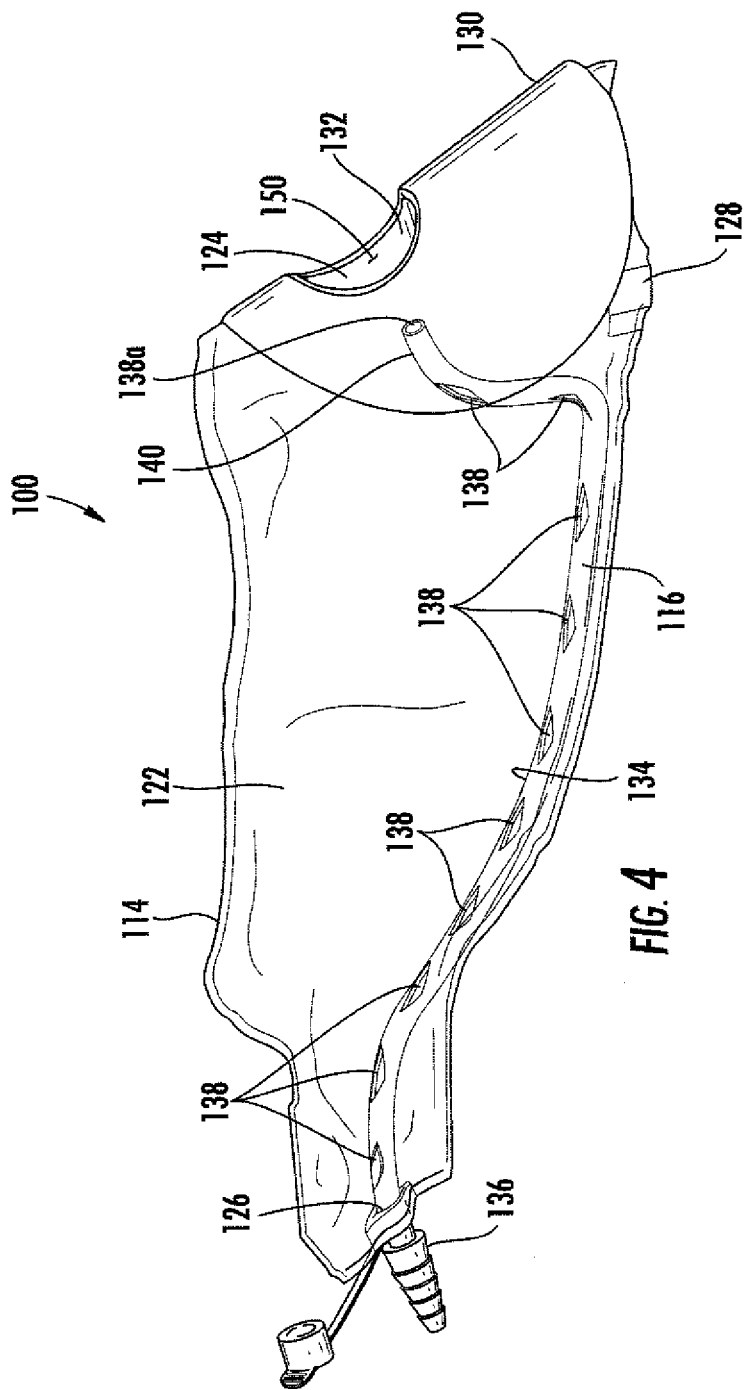
FIG. 4 is a perspective view of an alternative bodily waste collection system showing the terminal end of an evacuation conduit positioned near a wafer opening, in according with an exemplary embodiment of the present invention.

Referring to FIG. 4, an alternative embodiment of a non-invasive bodily waste collection system 100 is illustrated. The collection system 100 includes a collection bag 114 having an interior chamber 122, first and second openings 124, 126 and a sampling port 128; a wafer 130 attached to the bag 114 and having an orifice 132 that coincides with the first opening 124 of the bag 114 and; a suction tube 118 and a suction device 120 for removing waste from the bag 114. These elements are as described above in reference to the embodiment illustrated by FIGS. 1-3, the description of which is incorporated herein by reference.

The collection system 100 further includes an evacuation tube 116 having first and second sections 134, 136. The second section 136 is the same as that described in reference to the embodiment illustrated by FIGS. 1-3, whereas the first section 134 is similar to that of the previous embodiment but wherein the proximal end 140 of the second section 136 terminates near the collection bag first opening 124. The proximal end 150 is not directly attached to the collection bag 114 and, preferably, terminates about one to three inches, and more preferably one to two inches, from the center 150 of the first opening 124 thereby being sufficiently separated from the person's anus to avoid having the tube 116 engage against the person or having difficulties in attaching the collection bag 114 to the person.

Measured in percentages of length, at least a portion, more preferably at least 25%, even more preferably at least 50%, and most preferably at least 75% of the first section 134 is directly attached to the collection bag 114 in order to maintain the attached portion of the evacuation tube 116 in a fixed positioned relative to the collection bag 114. Although the proximal end 140 of the tube 116 is not directly attached to the bag 116, by fixing other portion(s) of the evacuation tube 116 to the collection bag 114, desired positioning of the tube 16 and its proximal end 140 may be maintained.

As with the embodiment of FIGS. 1-3, the first section 134 of the evacuation tube 116 is provided with at least one opening 138 and, more preferably a plurality of openings 138, which communicate with the interior chamber 122 of the bag 114 for receiving waste. In the preferred embodiment, the openings 138 comprise an opening 138a at the proximal end 140 of the evacuation tube 116 and openings 138 intermittently positioned along the length of the first section 134. The openings 138 may be of any suitable number, size or shape that allows for successful evacuate of waste from the collection bag 114.

Figure 5:
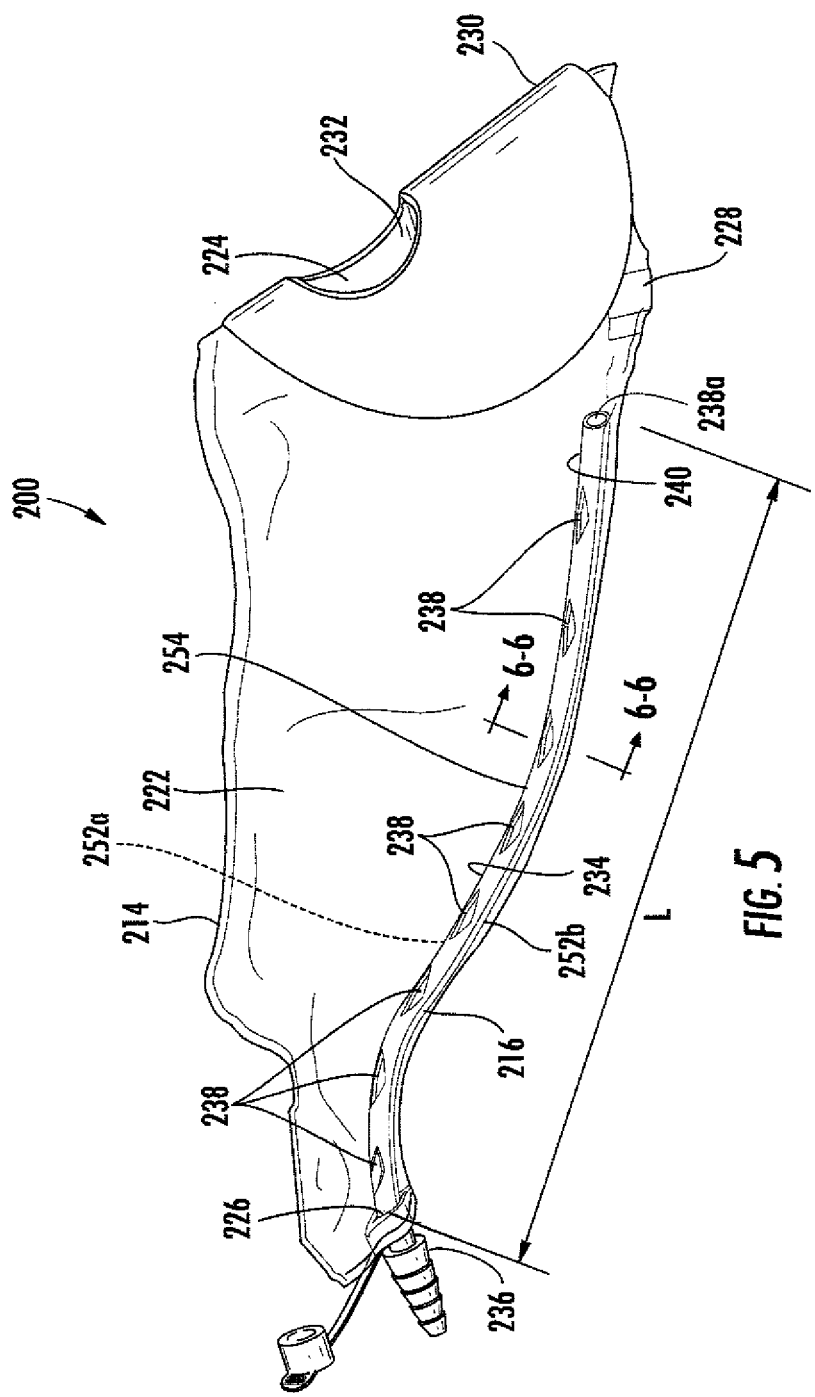
FIG. 5 is a perspective view of a further alternative bodily waste collection system, similar to the embodiment of FIG. 1, but wherein the system is configured to obviate fecal matter from collecting on the underside of the evacuation tube, in according with an exemplary embodiment of the present invention.
Figure 6:
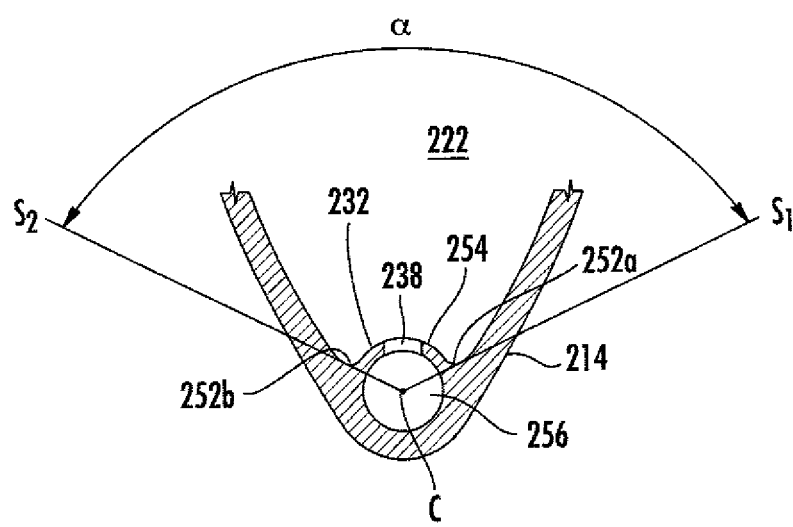
FIG. 6 is a partial cross-sectional view of the bodily waste collection system, taken from sectional line 6-6 of FIG. 5.

Referring to FIGS. 5 and 6, still another embodiment of a non-invasive bodily waste collection system 200 is illustrated. The collection system 200 includes a collection bag 214 having an interior chamber 222, first and second openings 224, 226 and a sampling port 228; a wafer 230 attached to the bag 214 and having an orifice 232 that coincides with the first opening 224 of the bag 214; and a suction tube (see e.g. FIG. 1, suction tube 18) and a suction device (see e.g. FIG. 1, suction device 20) for removing waste from the bag 214. These elements are the same as described above in reference to the embodiment illustrated by FIGS. 1-3, the description of which is incorporated herein by reference.

The collection system 200 further includes an evacuation tube 216 having first and second sections 234, 236. The second section 234 is the same as the embodiment illustrated by FIGS. 1-3, whereas the first section 234 is similar to that embodiment but wherein the evacuation tube 216 and collection bag 214 are attached together in such a manner that waste is blocked from getting under the tube 216. As such, it is less likely that waste will become trapped on otherwise remain in the bag 214 after suction by the suction device (see e.g. FIG. 1, suction device 20).

At least a portion, more preferably at least 50%, even more preferably at least 75%, and most preferably at least 90% of the first section 234 is directly attached to the collection bag 214 in order to maintain the attached portion of the evacuation tube 216 in a fixed positioned relative to the collection bag 214.

Additionally, it is preferred that attachment interfaces 252a, 252b between the tube 216 and bag 214 allows no more than about 90%, more preferably no more than about 75%, even more preferably no more than about 50%, and most preferably no more than about 33% of the outer surface area 254 of first section 234 of the tube 216 to be exposed to the interior chamber 222 of the bag 214. Attachment between the tube 216 and collection bag 214 may be achieved by any suitable method such as, for example, by use of an adhesive or by forming these components as one unitary integral piece.

Referring to FIG. 6, in calculating the percentage of outer surface area 254 of the first section 234 that is exposed to the interior chamber 222 of the bag, an angle ($\alpha$) is averaged along the length (L) (FIG. 5) of the first section 234 and divided by 360 degrees, as follows:

Exposed outer surface area %=$\alpha_{average}$/360 degrees

Angle ($\alpha$) is measured from a first segment line ($S_1$) drawn from the center point (C) of the tube's passageway 256 to first attachment interface 252a to the second segment line (S2) drawn from the center point (C) of the tube's passageway 256 to the second attachment interface 252b.

It is to be understood that different configurations of evacuation tubes and/or attachment interfaces may dictate that the exposed outer surface area of the first section be calculated in a different manner. Nevertheless, the principles of considering the amount of exposure area compared to the total area had the tube not been attached to the bag remain.

Referring to FIG. 5, as with the embodiment of FIGS. 1-3, the first section 234 of the evacuation tube 216 is provided with at least one opening 238 and, more preferably a plurality of openings 238, which communicate with the interior chamber 222 of the bag 214 for receiving waste. In the preferred embodiment, the openings 238 comprise an opening 238a at the proximal end 240 of the evacuation tube 216 and openings 238 intermittently positioned along the length of the first section 234. The openings 238 may be of any suitable number, size or shape that allows for successful evacuate of waste from the collection bag 214.

Figure 7:
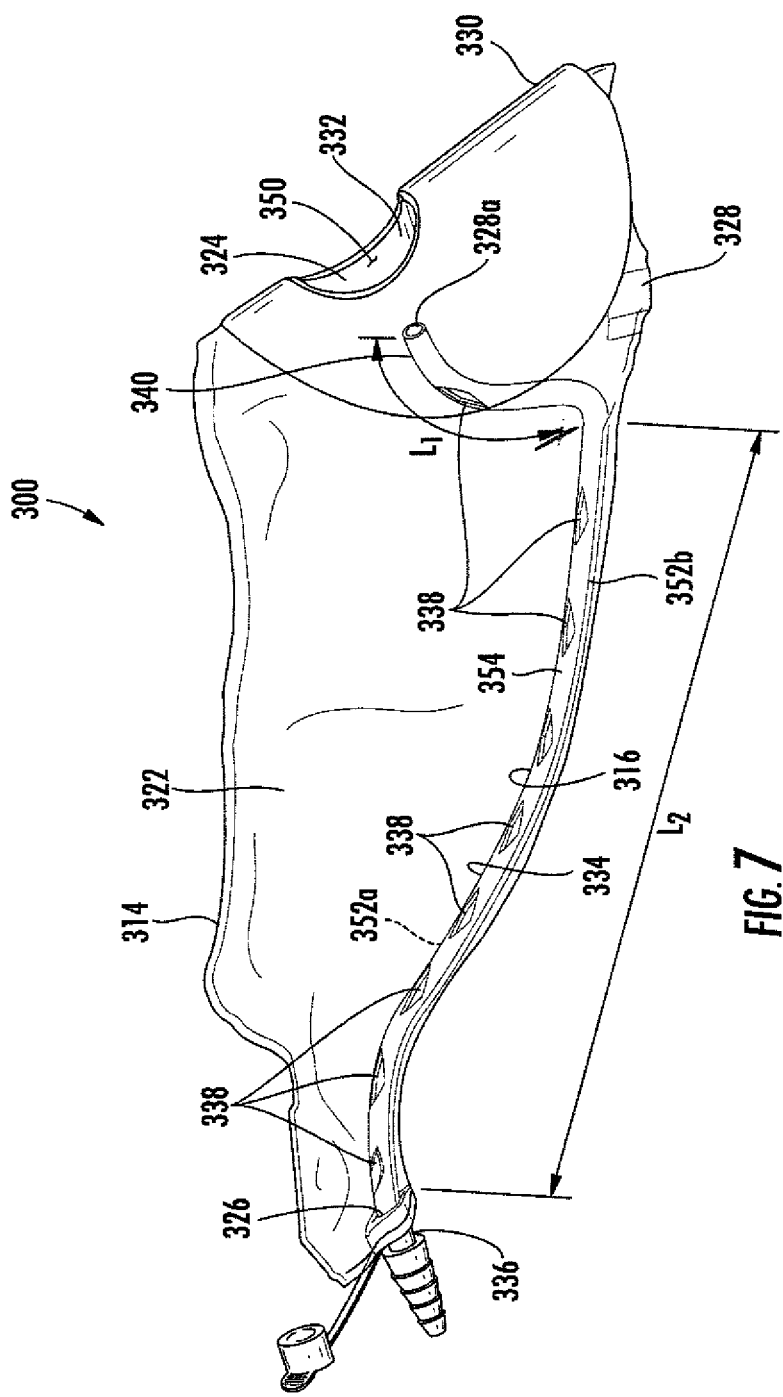
FIG. 7 is a perspective view of a further alternative bodily waste collection system, similar to the embodiment of FIG. 4, wherein the system is configured to obviate fecal matter from collecting on the underside of the evacuation tube, in according with an exemplary embodiment of the present invention.
Figure 8:
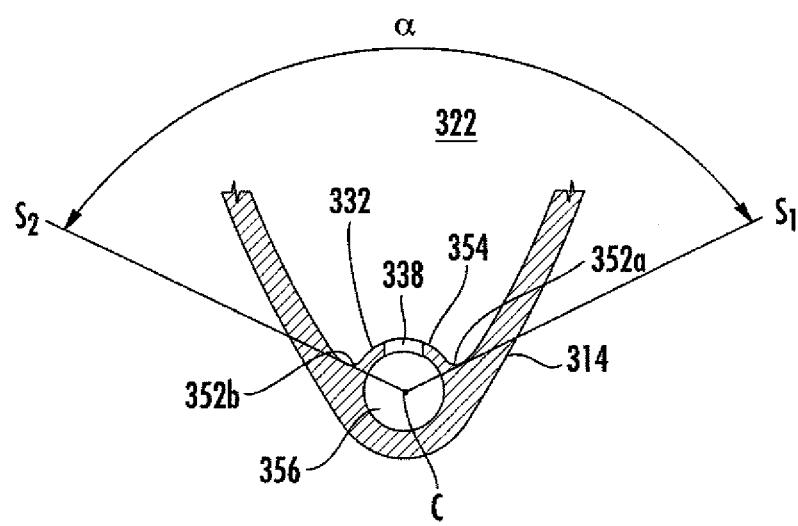
FIG. 8 is a partial cross-sectional view of the bodily waste collection system, taken from sectional line 8-8 of FIG. 7.

Referring to FIGS. 7 and 8, still another embodiment of a non-invasive bodily waste collection system 300 is illustrated. The collection system 300 includes a collection bag 314 having an interior chamber 322, first and second openings 324, 326 and a sampling port 328; a wafer 330 attached to the bag 314 and having an orifice 332 that coincides with the first opening 324 of the bag 314; and a suction tube (see e.g. FIG. 4, suction tube 18) and a suction device (see e.g. FIG. 4, suction device 20) for removing waste from the bag 314. These elements are the same as described above in reference to the embodiment illustrated by FIG. 4, the description of which is incorporated herein by reference.

The collection system 300 further includes an evacuation tube 316 having first and second sections 334, 336. The second section 336 is the same as that described in reference to the embodiment illustrated by FIG. 4, whereas the first section 334 is similar to that of the embodiment of FIG. 4 but wherein at least a portion of the evacuation tube 316 is directly attached to the collection bag 314 in a manner that waste is blocked from getting under the tube 316.

At least a portion, more preferably at least 50%, even more preferably at least 75% of the first section 334 is directly attached to the collection bag 314 in order to maintain the attached portion of the evacuation tube 316 in a fixed positioned relative to the collection bag 314. The proximal end 340 of the tube 316 remains free, i.e. only indirectly attached to the bag 316, so that it may be positioned within one to three inches, and more preferably one to two inches, from the center 350 of the first opening 324 of the bag 314.

Additionally, it is preferred that attachment interfaces 352a, 352b between the tube 316 and bag 314 allows no more than about 90%, more preferably no more than about 75%, even more preferably no more than about 50%, and most preferably no more than about 33% of the outer surface area 254 of first section 234 of the tube 316 to be exposed to the interior chamber 322 of the bag 314. Attachment between the tube 316 and collection bag 314 may be achieved by any suitable method such as, for example, by use of an adhesive or by forming these components as one unitary integral piece.

Referring to FIG. 8, in calculating the percentage of outer surface area 354 of the first section 334 that is exposed to the interior chamber 322 of the bag, an angle ($\alpha$) is averaged along a length ($L_2$) (FIG. 8) of the first section 334, (i.e. excluding the length $L_1$ of proximal end 340) and divided by 360 degrees, as follows:

Exposed outer surface area %=$\alpha_{average}$/360 degrees

Angle ($\alpha$) is measured from a first segment line ($S_1$) drawn from the center point (C) of the tube's passageway 356 to first attachment interface 352a to the second segment line (S2) drawn from the center point (C) of the tube's passageway 356 to the second attachment interface 352b.

It is to be understood that different configurations of evacuation tubes and/or attachment interfaces may dictate that the exposed outer surface area of the first section be calculated in a different manner. Nevertheless, the principles of considering the amount of exposure area compared to the total area had the tube not been attached to the bag remain.

As with the embodiment of FIGS. 1-3, the first section 334 of the evacuation tube 316 is provided with at least one opening 338 and, more preferably a plurality of openings 338, which communicate with the interior chamber 322 of the bag 314 for receiving waste. In the preferred embodiment, the openings 338 comprise an opening 338a at the proximal end 340 of the evacuation tube 316 and openings 338 intermittently positioned along the length of the first section 334. The openings 338, 338a may be of any suitable number, size or shape that allows for successful evacuate of waste from the collection bag 314.

Referring to FIG. 1, in use, the collection bag first opening 24 and wafer orifice 32 are simultaneously formed by cutting the orifice 32 and openings 24 to a proper size for the person 100 to which the device is to be applied. A protective release paper (not illustrated) is removed from the wafer 30 and the collection bag 10 is non-invasively attached to the peri-anal region of the person 100 by adhesive contact. The first opening 24 and wafer orifice 32 coincide with the person's anus to allow waste to pass into the collection bag 14.

To effectively empty collection bag 14, the suction device 20 provides vacuum pressure which causes waste to be drawn into the evacuation tube 16 through the openings 38, 38a, to the suction tube 18, then ultimately to the container 50 where it can be tested and/or disposed of. Accordingly, the collection bag 14 may be emptied and the waste stored away from the person 100 without requiring manual methods to remove the waste.

The foregoing provides a detailed description of exemplary embodiments of the present invention. Although specific embodiments of a noninvasive bodily waste collection system have been described with reference to preferred embodiments and examples thereof, other embodiments and examples may perform similar functions and/or achieve similar results. All such equivalent embodiments and examples are within the spirit and scope of the present invention and are intended to be covered by the following claims.

That which is claimed is:

1. A noninvasive bodily waste collection apparatus, comprising:
   a collection bag defining an interior chamber and having first and second openings;
   said collection bag being releasably attachable to a person whereby waste from said person is passed through said first opening and into said interior chamber;
   an evacuation tube having first and second sections, wherein said first section is positioned within said collection bag and at least a portion of said first section is directly attached to said collection bag whereby said at least a portion of said first section is fixed in position relative to said collection bag;
   said first section having at least one opening which communicates with said interior chamber for having waste pass from said interior chamber into said evacuation tube;
   said evacuation tube adapted for receiving vacuum pressure for drawing waste from said interior chamber into said evacuation tube, and wherein said at least a portion of said first section is at least 25% of said first section, measured as a percentage of length of said first section that is directly attached to said collection bag compared to total length of said first section.

2. The noninvasive bodily waste collection apparatus according to claim 1, wherein no more than about 90% of an outer surface area of said first section is exposed to said interior chamber.

3. The noninvasive bodily waste collection apparatus according to claim 1, wherein said at least a portion of said first section is at least 50% of said first section, measured as a percentage of length of said first section that is directly attached to said collection bag compared to total length of said first section.

4. The noninvasive bodily waste collection apparatus according to claim 1, wherein said at least a portion of said first section is at least 75% of said first section, measured as a percentage of length of said first section that is directly attached to said collection bag compared to total length of said first section.

5. The noninvasive bodily waste collection apparatus according to claim 1, wherein said at least one opening is a plurality of openings.

6. A noninvasive bodily waste collection apparatus, comprising:
   a collection bag defining an interior chamber and having first and second openings;
   said collection bag being releasably attachable to a person whereby waste from said person is passed through said first opening and into said interior chamber;
   an evacuation tube having first and second sections, wherein said first section is positioned within said collection bag and at least a portion of said first section is directly attached to said collection bag whereby said at least a portion of said first section is fixed in position relative to said collection bag;
   said first section having at least one opening which communicates with said interior chamber for having waste pass from said interior chamber into said evacuation tube;
   said evacuation tube adapted for receiving vacuum pressure for drawing waste from said interior chamber into said evacuation tube; and
   a wafer releasably attachable to a peri-anal region of said person by an adhesive.

7. The noninvasive bodily waste collection apparatus according to claim 1, wherein said first section includes a proximal end that is not directly attached to said collection bag and is positioned about one to three inches from a center of said first opening.

8. A noninvasive bodily waste collection apparatus, comprising:
   a collection bag defining an interior chamber and having first and second openings;
   said collection bag being releasably attachable to a person whereby waste from said person is passed through said first opening and into said interior chamber;
   an evacuation tube having first and second sections, wherein said first section is positioned within said collection bag and at least a portion of said first section is directly attached to said collection bag whereby said at least a portion of said first section is fixed in position relative to said collection bag;
   said first section having at least one opening which communicates with said interior chamber for having waste pass from said interior chamber into said evacuation tube;
   said evacuation tube adapted for receiving vacuum pressure for drawing waste from said interior chamber into said evacuation tube; and
   wherein said second section is disposed through said second opening of said collection bag and is releaseably attachable to a suction device that provides said vacuum pressure.

9. The noninvasive bodily waste collection apparatus according to claim 1, wherein said first section is unitary with said collection bag.

10. The noninvasive bodily waste collection apparatus according to claim 1, wherein no more than about 90% of an outer surface area of said first section is exposed to said interior chamber.

11. The noninvasive bodily waste collection apparatus according to claim 1, wherein no more than about 75% of an outer surface area of said first section is exposed to said interior chamber.

12. The noninvasive bodily waste collection apparatus according to claim 1, wherein no more than about 50% of an outer surface area of said first section is exposed to said interior chamber.

13. A noninvasive bodily waste collection system, comprising:
   a collection bag defining an interior chamber and having first and second openings;
   a wafer attached to said collection bag and having an orifice that coincides with said first opening, said wafer being releaseably attachable to a person at a position whereby waste from said person is passed through said first opening and said orifice and into said interior chamber;
   an evacuation tube having first and second sections, wherein said first section is positioned within said collection bag and at least portion of said first section is directly attached to said collection bag whereby said at least a portion of said first section is fixed in position relative to said collection bag;

said first section having at least one opening which communicates with said interior chamber for having waste pass from said interior chamber into said evacuation tube;

a suction tube attached to said second section; and a suction device attached to said suction tube for drawing waste from said interior chamber and through said evacuation tube and said suction tube.

14. The noninvasive bodily waste collection system according to claim 13, wherein said at least a portion of said first section is at least 25% of said first section, measured as a percentage of length of said first section that is directly attached to said collection bag compared to total length of said first section.

15. The noninvasive bodily waste collection apparatus according to claim 14, wherein no more than about 90% of an outer surface area of said first section is exposed to said interior chamber.

16. The noninvasive bodily waste collection apparatus according to 13 wherein said first section includes a proximal end that is not directly attached to said collection bag and is positioned about one to three inches from a center of said first opening.

17. The noninvasive bodily waste collection apparatus according to claim 13, wherein said at least one opening is a plurality of openings.

* * * * *